United States Patent

Negele et al.

[11] Patent Number: 5,109,020
[45] Date of Patent: Apr. 28, 1992

[54] FLUORINATED CYCLOHEXANE DERIVATIVES, PROCESS AND INTERMEDIATES FOR THEIR PREPARATION AND THE USE OF THE NEW FLUORINATED CYCLOHEXANE DERIVATIVES AS FUNGICIDES AND INTERMEDIATES

[75] Inventors: Michael Negele, Cologne; Bernd Baasner, Bergisch Gladbach, both of Fed. Rep. of Germany

[73] Assignee: Bayer Aktiengesellschaft, Leverkusen, Fed. Rep. of Germany

[21] Appl. No.: 549,784

[22] Filed: Jul. 9, 1990

[30] Foreign Application Priority Data

Jul. 22, 1989 [DE] Fed. Rep. of Germany ...... 3924304

[51] Int. Cl.$^5$ ............... C07C 255/46; C07C 211/35; C07C 211/40; A01N 37/34
[52] U.S. Cl. ...................... 514/519; 514/579; 514/659; 558/431; 564/462
[58] Field of Search ............ 564/462; 558/431; 514/579, 519, 659

[56] References Cited

U.S. PATENT DOCUMENTS 4,774,358 9/1988 Baasner .................... 564/1

FOREIGN PATENT DOCUMENTS 0244613 3/1987 European Pat. Off.
0317888 5/1989 European Pat. Off.
2630562 1/1978 Fed. Rep. of Germany
3808276 9/1989 Fed. Rep. of Germany

*Primary Examiner*—Joseph Paul Brust
*Attorney, Agent, or Firm*—Sprung Horn Kramer & Woods

[57] ABSTRACT

The present invention relates to new fluorinated cyclohexane derivatives of the formula

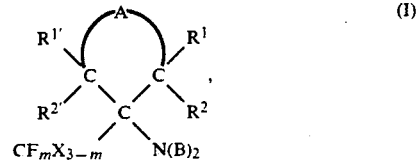

in which the symbols used have the meaning indicated in the description, a process for their preparation, intermediates of the formula

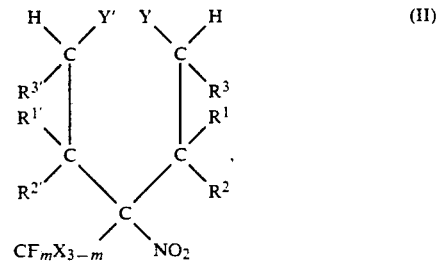

in which the symbols have the meaning indicated in the description, and the use of the new fluorinated cyclohexane derivatives as fungicides and intermediates.

3 Claims, No Drawings

FLUORINATED CYCLOHEXANE DERIVATIVES, PROCESS AND INTERMEDIATES FOR THEIR PREPARATION AND THE USE OF THE NEW FLUORINATED CYCLOHEXANE DERIVATIVES AS FUNGICIDES AND INTERMEDIATES

The present invention relates to new fluorinated cyclohexane derivatives, which contain at least one nitro group or amino group and which may be polysubstituted, a process and intermediates for their preparation and the use of the new fluorinated cyclohexane derivatives as fungicides, active compounds against livestock parasites and intermediates for the preparation of biologically active substances.

Processes are known in which fluoronitroalkanes of the type a)

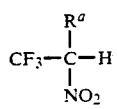
a)

are reacted with an α,β-unsaturated compound of the type b)

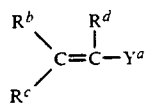
b)

in which $Y^a = COR^e$, $COOR^f$, CN, $NO_2$ or $SO_3R^g$, and fluorinated nitroalkyl compounds of the type c)

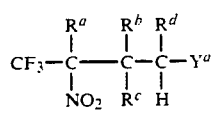
c)

are thus obtained. The reaction can take place in the presence of alkaline metal fluorides and an aprotic solvent (see DE-OS 3,739,784) or in the presence of aluminium oxide (see DE-OS 3,808,276). If fluoronitroalkanes of the type a) in which $R^a$ = hydrogen are used, it is also possible for 2 moles of the type b) compound to react with 1 mole of the type a) compound in an undesired manner. It is not stated which products are formed in this reaction.

New fluorinated cyclohexane derivatives of the formula (I) have now been found,

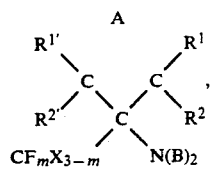
(I)

in which
  A represents one of the following $C_3$-alkylene radicals

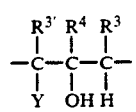
i)

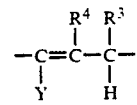
ii)

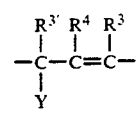
iii)

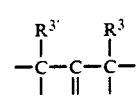
iv)

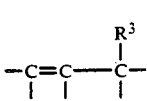
v)

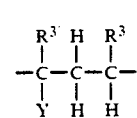
vi)

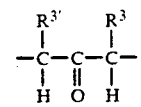
vii)

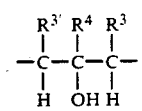
viii)

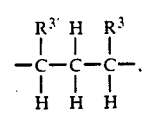
ix)

B represents oxygen or hydrogen,
X represents hydrogen, chlorine, bromine or methyl,
m represents 1, 2 or 3,
$R^1$, $R^2$, $R^3$, $R^{1'}$, $R^{2'}$ and $R^{3'}$ independently of one another in each case represent hydrogen, halogen, cyano, optionally substituted $C_1$- to $C_6$-alkyl or optionally substituted $C_6$- to $C_{10}$-aryl,
$R^4$ represents hydrogen, $C_1$- to $C_6$-alkyl or $C_6$- to $C_{10}$-aryl
and
Y
  represents a $COR^{4'}$ group in which $R^{4'}$ = hydrogen, $C_1$- to $C_6$-alkyl or $C_6$- to $C_{10}$-aryl (independently from $R^4$) or
  a $CO\text{-}OR^5$ group in which $R^5 = C_1$- to $C_6$-alkyl or $C_6$- to $C_{10}$-aryl or
  a $SO_2\text{-}OR^6$ group in which $R_6 = C_1$- to $C_6$-alkyl or $C_6$- to $C_{10}$-aryl or
  a cyano group or
  a nitro group.

Insofar as substituted alkyl and/or aryl radicals can be present as radicals in formula (I), suitable substituents are, for example, nitro, halogen, $C_1$- to $C_4$-alkoxy and cyano groups. Here halogen preferably represents fluorine, chlorine or bromine, particularly fluorine. Aromatic radicals are also suitable as substituents for alkyl radicals.

$R^1$ and $R^{1'}$ are preferably identical, independently from these $R^2$ and $R^{2'}$ are preferably identical and independently from these $R^3$ and $R^{3'}$ are preferably identical.

Fluorinated cyclohexane derivatives of the formula (I) are preferred, in which
A represents i), ii), iv), vii) or viii),
X represents hydrogen or chlorine,
m represents 2 or 3,
$R^1$, $R^2$, $R^3$, $R^{1'}$, $R^{2'}$ and $R^{3'}$ independently of one another in each case represent hydrogen, halogen, unsubstituted $C_1$- to $C_6$-alkyl or substituted $C_6$- to $C_{10}$-aryl,
Y
  represents a $COR^{4'}$ group in which $R^{4'}$ = hydrogen, $C_1$- to $C_6$-alkyl or $C_6$- to $C_{10}$-aryl (independently from $R^4$) or
  a $CO-OR^5$ group in which $R^5 = C_1$- to $C_6$-alkyl or $C_6$- to $C_{10}$-aryl or
  a cyano group.

Particularly preferred single compounds of formula (I) are those in which the substituents have the following meaning:
a) A=i), B=oxygen, m=3, $R^1=R^2=R^3=R^{1'}=R^{2'}=R^{3'}$=hydrogen, $R^4$=methyl and Y=$COCH_3$,
b) as a), but B=hydrogen,
c) as a), but Y=cyano,
d) A=ii), B=oxygen, m=3, $R^1=R^2=R^3=R^{1'}=R^{2'}=R^{3'}$=hydrogen, $R^4$=hydrogen and Y=CHO,
e) as d), but $R^4$=methyl,
f) A=iv), B=oxygen, m=3, $R^1=R^2=R^3=R^{1'}=R^{2'}=R^{3'}$=hydrogen and Y=-$COOCH_3$ and
g) A=ix), B=hydrogen, m=3 and $R^1=R^2=R^3=R^{1'}=R^{2'}=R^{3'}$=hydrogen.

The new fluorinated cyclohexane derivatives of the formula (I) can in each case exist as a single structural isomer, but also as any mixture of different structural isomers.

The new fluorinated cyclohexane derivatives of the formula (I) are biologically active compounds and/or intermediates for the preparation of biologically active compounds. Here biologically active means, for example, that the compounds exhibit a good plant protecting fungicidal effect with good toleration by plants. They are particularly effective in combating the causative organism of apple scab.

The good toleration by plants of the fluorinated cyclohexane derivatives according to the invention, at the concentrations required for combating plant diseases, permits treatment of above-ground parts of plants, of vegetative propagation stock and seeds, and of the soil. The active compounds can be converted into the customary formulations, such as solutions, emulsions, suspensions, powders, foams, pastes, granules, aerosols, very fine capsules in polymeric substances and in coating compositions for seeds, as well as ULV formulations.

These formulations can be produced in a known manner, for example by mixing the active compounds with extenders, for example, liquid solvents, liquified gases under pressure and/or solid carriers, optionally with the use of auxiliaries such as surface-active agents, emulsifying agents, dispersing agents, and/or foam-forming agents. In the case of the use of water as extender, organic solvents can, for example, also be used as auxiliary solvents. Suitable liquid solvents are, for example, aromatics, chlorinated aromatics, chlorinated aliphatic hydrocarbons, aliphatic hydrocarbons, alcohols, ethers, esters, ketones, dimethylformamide, dimethylsulphoxide and/or water. By liquified gaseous extenders or carriers are meant those liquids which are gaseous under atmospheric pressure and at ambient temperature, for example aerosol propellants, such as lower halogenated hydrocarbons, butane, propane, nitrogen and carbon dioxide. Suitable solid carriers are, for example, ground natural minerals, ground synthetic minerals, highly-dispersed silica, alumina and silicates. Furthermore of interest as solid carriers for granules are crushed and fractionated natural rocks as well as synthetic granules of inorganic and organic meals, and granules of organic material such as sawdust, coconut shells, maize cobs or tobacco stalks. Suitable emulsifying and/or foam-forming agents are, for example, non-ionic and anionic emulsifiers, and suitable dispersing agents are lignin-sulphite waste liquors and methylcellulose.

Adhesives such as carboxymethylcellulose can also be used in the formulations.

The formulations can contain, for example, 0.1 to 95% by weight of active compound, preferably 0.5 to 90% by weight. The active compounds according to the invention can be present in the formulations as a mixture with other known active compounds, for example, in combination with other fungicides, insecticides, acaricides and herbicides, as well as in mixtures with fertilizers and growth regulators.

The active compounds can be used as such or in the form of their formulations or the use forms prepared therefrom, such as ready-to-use solutions, emulsifiable concentrates, emulsions, foams, suspensions, wettable powders, pastes, soluble powders, dusts and/or granules. They can be used, for example, by watering, spraying, atomizing, scattering, dusting, foaming or brushing on. It is furthermore possible to apply the active compounds by the ultra-low volume (ULV) method or to inject the active compound formulation or the active compound itself into the soil. The seeds of the plants can also be treated.

In the treatment of parts of plants, the active compound concentrations in the use forms can be varied within a substantial range. They are, in general, between 1 and 0.0001% by weight, preferably between 0.5 and 0.001% by weight.

In the treatment of seed, amounts of active compound of 0.001 to 50 g/kg of seed, preferably 0.01 to 10 g/kg of seed are generally used.

For the treatment of soil, active compound concentrations in the range of 0.0001 to 0.1% by weight, preferably 0.0001 to 0.02% by weight can be used at the place of action.

Insofar as new fluorinated cyclohexane derivatives of the formula (I) are used as intermediates for the preparation of biologically active compounds it is possible, for example, from these, to prepare carbamates by reaction with esters of chloroformic acid, or ureas by reaction with isocyanates, said carbamates and ureas possessing insecticidal or herbicidal activity.

Furthermore the present invention relates to a process for the preparation of fluorinated cyclohexane derivatives of the formula (I), which is characterized in that, a compound of the formula (II)

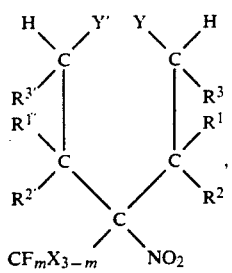

in which
X, m, $R^1$, $R^2$, $R^3$, $R^{1'}$, $R^{2'}$, $R^{3'}$ and Y have the meaning indicated for formula (I) and
Y' represents a $COR^4$, $CO-OR^5$ or cyano group (where $R^4$ and $R^5$ are defined as for Y),
is cyclized in the presence of a base and where appropriate the product is then converted into another derivative.

Suitable bases are the most diverse compounds having a basic action, for example alkali metal fluorides in an aprotic solvent, hydroxides, carbonates, alcoholates, hydrides and amides of alkali metals and alkaline earth metals, organic bases such as tetraalkylammonium hydroxides and anion exchange resins in basic form. Reaction conditions for the cyclization reaction are, for example, temperatures in the range from $-78°$ to $+150°$ C., reaction times in the range from 6 to 48 hours and the presence of one or more solvents. Preferably the temperature is in the range 0° to 82° C. and the solvent is acetonitrile.

The cyclization reaction proceeds particularly simply if Y and/or Y' in the compound of the formula (II) which is used represents a $COR^4$ group and it is desired to obtain compounds of the formula (I) in which A=i). In this case it is generally sufficient, in the preparation of the compound of the formula (II) described further below, to stir the reaction mixture longer and/or at a higher temperature than usual, for example, overnight (about 18 hours) in refluxing acetonitrile. The presence of an alkali metal fluoride and an aprotic solvent then already suffices to obtain the indicated compounds of the formula (I) in which A=i) without any problem and without conversion to another derivative.

If it is desired to carry out the cyclization with bases other than an alkali metal fluoride in an aprotic solvent, it is advantageous when preparing the compound of the formula (II) to isolate the latter and to carry out the cyclization reaction separately from the preparation of the compound of formula (II).

If strong bases are used, for example, concentrated alkali metal hydroxide solutions, alcoholates, amides or hydrides, and/or Y or Y' in the compound of the formula (II) used represents a strongly activating radical such as $COOR^5$, CN or CHO, a dehydration generally takes place after the cyclization. Compounds of the formula (I) in which A=ii) or iii) are then obtained. Compounds of the formula (I) in which A=ii) are preferentially obtained if a compound of the formula (II) is used in which $R^{3'}$=hydrogen and compounds of the formula (I) in which A=iii) are generally obtained if a compound of the formula (II) is used in which $R^{3'}\neq$hydrogen and $R^3$ represents a dehydration promoting group, for example an aryl or cyano group.

Compounds of the formula (I) in which A=iv) and Y=$COOR^5$ can be obtained if a compound of the formula (II) in which Y=Y'=$COOR^5$ is reacted with a stoichiometric amount of alkali metal alcoholate and the product is then hydrolysed. If, additionally, a decarboxylation is carried out, for example by acid hydrolysis at elevated temperature, compounds of the formula (I) in which A=vii) can also be obtained.

Compounds of the formula (I) in which A=v) can be obtained if a compound of the formula (II) in which Y=Y'=CN and $R^{3'}$=hydrogen is cyclized with a strong base, for example a hydride or amide, at high dilution in an inert solvent, for example in a dialkyl ether or cyclic ether. A subsequent acid hydrolysis can then yield compounds of the formula (I) in which A represents iv) in which Y=CN and $R^{3'}$=hydrogen.

In all cyclization and derivative conversion reactions described hitherto compounds of the formula (I) in which B=oxygen are obtained. The corresponding compounds in which B=hydrogen can be obtained from these by a hydrogenation.

Such a hydrogenation can, for example, be carried out catalytically with hydrogen or by reaction with metal hydrides. The catalytic hydrogenation with hydrogen can be carried out in the presence or absence of solvents. In general it is advantageous to operate in the presence of a solvent, since a better control of the exothermic hydrogenation is then possible.

Suitable solvents are, for example, inert organic solvents. Suitable solvents are, for example, alcohols such as methanol, ethanol, ethylene glycol and diethylene glycol, ethers such as dioxane, tetrahydrofuran, ethylene glycol monomethyl ether, ethylene glycol monoethyl ether, ethylene glycol dimethyl ether, diethylene glycol monoethyl ether and diethylene glycol dimethyl ether, saturated hydrocarbons such as cyclohexane and esters such as ethyl acetate. Preferred solvents are methanol and ethanol. In the catalytic hydrogenation the hydrogen pressure can vary within wide limits. Pressures in the range from 1 to 30 bar, particularly 5 to 20 bar, are preferred. The reaction temperature can also be varied within wide limits, for example between 0° and 120° C. preferably between 10° and 80° C. For the hydrogenation of 1 mol of a compound of the formula (I) in which B=oxygen to the corresponding compound in which B=hydrogen, it is generally advantageous to use at least 3 mols of hydrogen. Suitable catalysts for the catalytic hydrogenation with hydrogen are, for example, those which consist of or contain metals and/or compounds of elements of subgroup 8 of the Periodic System of the Elements. In this context the metals ruthenium, rhodium, palladium, platinum, cobalt and nickel and their compounds are preferred. Such metals and metal compounds can also be applied to carrier materials. Metallic catalysts can also be used as Raney-type skeleton catalysts. Suitable catalyst quantities are, for example, those of from 0.1 to 15% by weight, relative to the compound of the formula (I) in which B=oxygen which is used.

Parallel to the previously described hydrogenation of a compound of the formula (I) in which B=oxygen to the corresponding compound in which B=hydrogen, further reactions can take place or be suppressed. Such further reactions can involve, for example, a conversion of an existing carbonyl group in the molecule segment A to a hydroxyl group and/or the hydrogenation of an existing double bond in the molecule segment A.

The corresponding carboxylic acids can be prepared from compounds of the formula (I) in which Y=$COOR^5$ or CN by acid hydrolysis under mild conditions (for example, temperature below 60° C.) and corresponding compounds of the formula (I) in which A=-viii) can be obtained from these acids by decarboxylation.

The corresponding hydrazones can be prepared from compounds of the formula (I) in which a central carbonyl group is present in the molecule segment A by reaction with hydrazine, and from these hydrazones, by elimination of nitrogen under the influence of strong bases and, if appropriate, elevated temperatures, compounds of the formula (I) in which A=ix) and B=hydrogen can be obtained which contain a methylene group instead of the original carbonyl group and in which the nitro group has been reduced to an amino group.

The compounds of formula (II) required as starting compounds for the preparation of the new fluorinated cyclohexane derivatives of the formula (I) are also new and can be obtained by reacting 1 mol of the fluoronitroalkane of the formula (III)

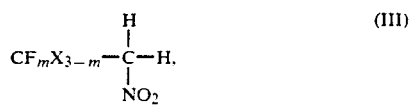

in which

X and m have the meaning indicated for formula (I), in the presence of alkali metal fluorides and a polar, aprotic solvent with at least 2 moles of one or more $\alpha,\beta$-unsaturated compounds of the formula (IV)

in which $R^1$ $R^2$, $R^3$ and Y have the meaning indicated for formula (I).

In contrast to DE-OS 3,739,784, in the above process, for example, the compound of the formula (IV) is initially introduced in an excess of at least 2 moles and is reacted with 1 mole of a compound of the formula (III) at low temperature, for example, at $-78°$ to $+10°C.$, preferably at 0° to 10° C. If necessary, the reaction mixture can subsequently be stirred at elevated temperature, for example at 50° to 100° C., preferably at 70° to 85° C., in order to bring the reaction to completion.

If several $\alpha,\beta$-unsaturated compounds of the formula (IV) are used, in particular two such compounds in succession, unsymmetrical compounds of the formula (II) can be obtained, i.e. compounds of the formula (II) in which $R^1$ and $R^{1'}$, $R^2$ and $R^{2'}$, $R^3$ and $R^{3'}$ and/or Y and Y' respectively differ from each other.

A particular procedure for the preparation of compounds of the formula (II) consists in first preparing, in accordance with DE-OS, a compound of the formula (III')

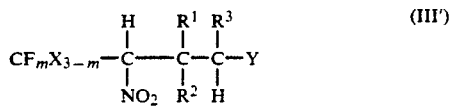

(the meanings of X, m, $R^1$, $R^2$ and $R^3$ are as indicated for formula (I)) purifying this and then, in a second stage, reacting it with a compound of the formula (IV).

It is extremely surprising that it was possible with the new fluorinated cyclohexane derivatives of the formula (I) to make available a new class of compounds having biological activities, since neither the activities of the substances of the new class of compounds nor their ready accessibility could be expected from the prior art described in the introduction.

EXAMPLES

Example 1

Preparation of dimethyl 4-trifluoromethyl-4-nitropimelate (formula (II), m=3, $R^1=R^2=R^3=R^{1'}=R^{2'}=R^{3'}$=hydrogen, Y=Y'=COOCH$_3$)

27 g (0.465 mol) of anhydrous potassium fluoride and 86 g (1.0 mol) of methyl acrylate were initially introduced into 150 ml of acetonitrile at 5° C. and 60 g (0.465 mol) of trifluoronitroethane were added slowly dropwise, with stirring, in the course of one hour. After the temperature had risen to 60° C., stirring was continued at room temperature for a further 3 hours. The mixture was then filtered and the residue washed with 100 ml of acetonitrile. The solvent and unconverted feed material were stripped from the combined filtrates under a water vacuum (12 mbar) and the residue (98 g) subjected to fractional distillation at 0.05 mbar. 86 g of product (=61% of theory) with a boiling point of 124° to 127° C. at 0.05 mbar were obtained. The $^1$H-NMR spectrum showed characteristic bands at $\delta=2.38$ to 2.61 ppm (m, 8H, 4CH$_2$) and 3.69 ppm (s, 6H, 2OCH$_3$) measured against tetramethylsilane as internal standard The $^{19}$F-NMR spectrum showed a characteristic band at $\delta=+7.5$ ppm (s, CF$_3$) measured against CF$_3$COOH as external standard.

Example 2

Preparation of 4-trifluoromethyl-4-nitropimelic acid dinitrile (formula (II), m=3, $R^1=R^2=R^3=R^{1'}=R^{2'}=R^{3'}$=hydrogen, Y=Y'=CN)

The procedure was as in Example 1, except that 53 g (1.0 mol) of acrylonitrile were used instead of 86 g of methyl acrylate. The working-up gave 75 g (=68% of theory) of product with a boiling point of 115° to 118° C. at 0.05 mbar.

The $^1$H-NMR spectrum showed characteristic bands at $\delta=2.54$ to 2.78 ppm (m, 8H, 4CH$_2$) measured against tetramethylsilane as internal standard. The $^{19}$F-NMR spectrum showed a characteristic band at $\delta=+10.4$ ppm (s, CF$_3$) measured against CF$_3$COOH as external standard.

Example 3

Preparation of methyl 4-trifluoromethyl-4-nitro-7-oxopelargonate (formula (II) m=3, $R^1=R^2=R^3=R^{1'}=R^{2'}=R^{3'}$=hydrogen, Y=COOCH$_3$, Y'=COCH$_3$)

43 g (0.2 mol) of methyl 4-trifluoromethyl-4-nitrovalerate and 5.8 g (0.1 mol) of anhydrous potassium fluoride were initially introduced into 75 ml of acetonitrile at 5° C. and 17.5 g (0.25 mol) of methyl vinyl ketone were added slowly with stirring. The mixture warmed to 50° C. and was then stirred for a further 4 hours at room temperature. The mixture was then filtered, the residue washed with 20 ml of acetonitrile, and the filtrate and the wash liquid were combined. The solvent and unconverted methyl vinyl ketone were stripped from this mixture under a water pump vacuum (12 mbar), the residue was taken up in 50 ml of methylene chloride, the mixture was washed successively with 50 ml of water, 25 ml of 5% by weight aqueous hydrochloric acid and a further 50 ml of water and dried over sodium sulphate, the solvent was stripped off and the residue was distilled under an oil pump vacuum. 38 g of product (=67% of theory) with a boiling point of 102° to 105° C. at 0.05 mbar were obtained.

The $^1$H-NMR spectrum showed characteristic bands at $\delta=2.18$ ppm (s, 3H, CH$_3$), 2.41 to 2.68 ppm (m, 8H, 4CH$_2$) and 3.72 ppm (s, 3H, OCH$_3$) measured against tetramethylsilane as external standard.

Example 4

Preparation of 4-trifluoromethyl-4-nitro-7-oxocaprylic acid nitrile (formula (II), m=3, $R^1=R^2=R^3=R^{1'}=R^{2'}=R^{3'}=$hydrogen, Y=CN, Y'=CHO)

37 g (0.2 mol) of 4-trifluoromethyl-4-nitrovaleronitrile and 5.8 g (0.1 mol) of anhydrous potassium fluoride were initially introduced into 75 ml of acetonitrile at 5° C. and 14 g (0.25 mol) of acrolein were added slowly, with stirring. The mixture warmed to about 40° C. and was then stirred for a further 3 hours at room temperature. The mixture was then filtered off, the residue was washed with 20 ml of acetonitrile, the filtrate and the wash liquid were combined and the solvent and unconverted acrolein were stripped from this mixture under a water pump vacuum (12 mbar). The residue was then taken up in 50 ml of methylene chloride, the mixture was washed successively with 50 ml of water, 25 ml of 5% by weight aqueous hydrochloric acid and a further 50 ml of water and dried over sodium sulphate. After stripping off the solvent, the residue was distilled under an oil pump vacuum. 32 g of product (=72% of theory) with a boiling point of 110° to 112° C. at 0.05 mbar were obtained.

Example 5

Preparation of 1-methyl-2-acetyl-4-trifluoromethyl-4-nitro-cyclohexan-1-ol (formula (I), m=3, B=oxygen, $R^1=R^2=R^{1'}=R^{2'}=$hydrogen, A=i) in which $R^3=R^{3'}=$hydrogen, $R^4=$CH$_3$ and Y=COCH$_3$)

27 g (0.465 mol) of anhydrous potassium fluoride and 70 g (1.0 mol) of methyl vinyl ketone were initially introduced into 150 ml of acetonitrile at 5° C. and 60 g (0.465 mol) of trifluoronitroethane were added dropwise, with stirring, in the course of 1 hour. The reaction mixture warmed to 70° C. and was then stirred for a further 4 hours at room temperature. According to gas chromatographic analysis, the reaction mixture then contained 5-trifluoromethyl-5-nitrononane-2,8-dione (formula (II), m=3, $R^1=R^2=R^3=R^{1'}=R^{2'}=R^{3'}=$hydrogen, Y=Y'=COCH$_3$)

After a further 5 hours stirring at 80° C. this product was completely cyclized to the product named in the title. The reaction mixture was then filtered off, the residue was washed with 100 ml of acetonitrile, the filtrate and the wash liquid were combined and the solvent and unconverted starting material were stripped off under a water pump vacuum. The residue was dissolved in 200 ml of methylene chloride, the solution was washed with 100 ml of water, then with 50 ml of 5% by weight aqueous hydrochloric acid and then with a further 100 ml of water and dried over sodium sulphate, the solvent was stripped off and an oily residue was thus obtained, which was distilled under an oil pump vacuum. 80 g of product (=64% of theory) with a boiling point of 112° to 115° C. at 0.5 mbar were obtained. The material in the receiver solidified gradually and had a melting point of 86° to 87° C.

The nuclear magnetic resonance spectra recorded gave the following characteristic data:

$^1$H-NMR $\delta=1.18$ ppm (s, 3H, CH$_3$); 1.24 ppm (dd, 1H, CH$_2$, $^2$J(H-H)=14.2 Hz, $^3$J(H-H)=4.7 Hz, $^4$J(H-H)=3.2 Hz); 1.82 ppm (dt, 1H, CH$_2$, $^2$J(H-H)=14.2 Hz, $^3$J(H-H)=4.1 Hz); 2.20 ppm (s, 3H, CH$_3$); 2.43 ppm (dd, 1H, CH, $^3$J(H-H)=13.5 Hz and 4.8 Hz); 2.54–2.77 ppm (dt, and dq, 4H, 2CH$_2$); 3.81 ppm (d, 1H, OH, $^4$J(H-H)=3.2 Hz) measured against tetramethylsilane as internal standard.

$^{13}$C-NMR (proton-decoupled, assignment confirmed by DEPT experiment): $\delta=23.4$ ppm (CH$_2$); 26.3 ppm (CH$_2$); 28.1 ppm (CH—C=O—); 31.3 ppm (CH$_3$—C—OH); 34.5 ppm (CH$_2$); 52.4 ppm (CH); 67.9 ppm (—C—OH; 91.1 ppm (CF$_3$—C—NO$_2$, J(C—F)=27 Hz); 122.7 ppm (CF$_3$, J(C—F)=284 Hz); 211.5 ppm (C=O) measured against tetramethylsilane as internal standard.

$^{19}$F-NMR: $\delta=+1.0$ ppm (s) measured against CF$_3$COOH as external standard.

Example 6

Preparation of 1-methyl-2-acetyl-4-amino-4-trifluoromethylcyclohexan-1-ol (formula (I) in which m=3, B=hydrogen, $R^1=R^2=R^{1'}=R^{2'}=$hydrogen and A=i) in which $R^3=R^{3'}=$hydrogen, $R^4=$CH$_3$ and Y=COCH$_3$ 27 g (0.1 mol) of the product prepared in accordance with Example 5 were hydrogenated in 100 ml of methanol in a stainless steel autoclave at 50° to 70° C. and under a hydrogen pressure of 50 to 60 bar for 6 hours over 3 g of palladium-on-charcoal (containing 5% by weight palladium). For working up, the hydrogenation mixture was filtered and the solvent was stripped from the filtrate under a water pump vacuum.

The remaining residue was distilled under an oil pump vacuum and 15 g (=63% of theory) of the product with a boiling point of 68° to 71° C. at 0.05 mbar were obtained.

The $^1$H-NMR spectrum showed characteristic bands at $\delta=1.23$ ppm (s, 3H, CH$_3$—C—OH); about 1.25 ppm (s, br, 2H, NH$_2$); 1.32 to 2.08 ppm (several m, 6H, 3CH$_2$); 2.28 ppm (s, 3H, CH$_3$—C=O); about 3.82 ppm (s, br, 1H, OH) measured against tetramethylsilane as internal standard.

The $^{19}$F-NMR spectrum showed a characteristic band at $\delta=-6.3$ ppm (s, CF$_3$) measured against CF$_3$COOH as external standard.

Example 7

Preparation of 1-formyl-3-trifluoromethyl-3-nitrocyclohex-1-ene (formula (II) in which m=3, B=oxygen, $R^1=R^2=R^{1'}=R^{2'}=$hydrogen and A=ii) in which Y=COR$^{4'}$ and $R^3=R^4=R^{3'}=R^4=$hydrogen)

27 g (0.465 mol) of anhydrous potassium fluoride and 56 g (1.0 mol) of acrolein were initially introduced into 50 ml of acetonitrile at 50° C. and 60 g (0.465 mol) of trifluoronitroethane were added dropwise, with stirring, in the course of 1 hour. The mixture warmed to 80° C. and was then stirred for a further 3 hours at room temperature. According to examination by gas chromatography the reaction mixture then contained a 4:1 mixture of 4-trifluoromethyl-4-nitroheptane-1,7-dial (formula (II) in which m=3, Y=Y'=CHO, all other substituents=hydrogen) and 2-formyl-4-trifluoromethyl-4-nitrocyclohexan-1-ol) (formula (I) in which m=3, B=oxygen, $R^1=R^2=R^{1'}=R^{2'}$=hydrogen and A=i) with Y=CHO, $R^3=R^4=R^{3'}=R^{4'}$=hydrogen).

The reaction mixture was stirred for a further 5 hours at 80° C. Ring closure to form 2-formyl-4-trifluoromethyl-4-nitrocyclohexan-1-ol was then complete.

The mixture was then filtered off, the residue was washed with 100 ml of acetonitrile, the filtrate and the wash liquid were combined and the solvent and unconverted starting material were stripped off under a water pump vacuum. The residue then remaining was dissolved in 200 ml of methylene chloride, the solution was washed with 100 ml of water, then with 50 ml of 5% by weight aqueous hydrochloric acid and then with a further 100 ml of water and dried over sodium sulphate. After stripping off the solvent under a water pump vacuum, 90 g of an oil remained, which according to examination by gas chromatography consisted to 80% of 2-formyl-4-trifluoromethyl-4-nitrocyclohexan-1-ol and to 20% of the corresponding dehydrated product (see title). During distillation of this oil complete dehydration to the product quoted in the title took place under the action of heat. This product was obtained in a yield of 51 g (=49% of theory), with a boiling point of 86° to 91° C. at 0.05 mbar.

The following shifts and coupling constants were determined from the recorded $^1$H-NMR spectrum ($^1$H-$^1$H coupling constants J(Hz) in CDCl$_3$+DMSO-d$_6$, measured at 360.116 MHz)

| Shifts δ (ppm) | Coupling constants J (Hz) |
| --- | --- |
| H at C-2 = 6.883 | $J_{24e}$ = 2.26; $J_{23e'}$ = 2.19; $J_{23a'}$ = 2.85 |
| $H_{3e'}$ = 2.705 | $J_{3e'3a'}$ = (−) 18.33; $J_{3e'4e}$ = 2.26 |
| $H_{3a'}$ = 2.495 | $J_{3a'4e}$ = 6.26 |
| $H_{4e}$ = 2.883 | $J_{4e4a}$ = (−) 14.30 |
| $H_{4a}$ = 2.163 | $J_{4a3a'}$ = 10.93; $J_{4a3e'}$ = 6.74 |
| $H_{6e'}$ = 3.638 | $J_{6e'6a'}$ = (−) 18.25 |
| $H_{6a'}$ = 2.661 | $J_{6e'2}$ = 2.34 |
| H at C-7 = 9.488 | |

The measurements were carried out against tetramethylsilane as internal standard.

The recorded $^{19}$F-NMR spectrum showed a characteristic band at δ= +1.8 ppm (s, CF$_3$) measured against CF$_3$COOH as external standard.

Example 8

Preparation of 1-methyl-2-formyl-4-trifluoromethyl-4-nitrocyclohex-1-ene (formula (II), m 3, B=oxygen, $R^1=R^2=R^{1'}=R^{2'}$=hydrogen and A=ii) in which Y=COR$^{4'}$, $R^3=R^{4'}=R^{3'}$=hydrogen and R$^4$=methyl)

40 g (0.2 mol) of 4-trifluoromethyl-4-nitrobutan-2-one and 5.8 g (0.1 mol) of anhydrous potassium fluoride were initially introduced into 75 ml of acetonitrile at 5° C. and 14 g (0.25 mol) of acrolein were added slowly, with stirring. The reaction mixture warmed to 40° C. and was then stirred for a further 3 hours at room temperature.

According to examination by gas chromatography, the reaction mixture then contained essentially 4-trifluoromethyl-4-nitrooctan-7-on-1-al (formula (II) m=3, Y=CHO, Y'=COCH$_3$ and all other substituents=hydrogen.

This product was converted to 1-methyl-2-formyl-4-trifluoromethyl-4-nitrocyclohexan-1-ol by stirring for a further 5 hours at 80° C.

The reaction mixture was then filtered off, the residue was washed with 50 ml of acetonitrile and the solvent and unconverted acrolein were stripped from the filtrate, combined with the wash liquid, under a water pump vacuum. The remaining residue was dissolved in 200 ml of methylene chloride, and the solution was washed with 100 ml of water, then with 50 ml of 5% by weight hydrochloric acid and then with a further 100 ml of water and dried over sodium sulphate. After stripping off the solvent, the oily residue was distilled under an oil pump vacuum, during which a dehydration took place to give the product named in the title. 22 g of product (=43% of theory) with a boiling point of 90° to 94° C. at 0.05 mbar were obtained.

The $^1$H-NMR spectrum showed characteristic bands at δ=2.16 ppm (s, 3H, CH$_3$); 2.38 to 2.91 ppm (m, 5H, CH$_2$); 3.66 ppm (dm, 1H, CH$_2$) and 10.5 ppm (s, 1H, CHO) measured against tetramethylsilane as internal standard.

The $^{19}$F-NMR spectrum showed a characteristic band at δ= +1.3 ppm (s, CF$_3$) measured against CF$_3$COOH as external standard.

Example 9

Preparation of 2-(methyloxycarbonyl)-4-trifluoromethyl-4-nitrocyclohexan-1-one (formula (I) in which m=3, B=oxygen, $R^1=R^2=R^{1'}=R^{2'}$=hydrogen and A=iv) in which Y=COOCH$_3$, $R^3=R^{3'}$=hydrogen)

30 g (0.1 mol) of the product from Example 1 were initially introduced into 100 ml of absolute methanol at room temperature and 18 g of a 30% by weight solution of sodium methylate in methanol (=0.1 mol of sodium methylate were added dropwise with stirring and ice-cooling. After no further heat of reaction was liberated, the mixture was stirred overnight at room temperature. 6 g of glacial acetic acid were then added to the reaction mixture for hydrolysis and the resulting mixture was then stirred into 200 ml of water. This mixture was extracted 3 times with 100 ml of diethyl ether on each occasion, and the combined ether phases were washed with water and dried over sodium sulphate. The ether was then stripped off under a water pump vacuum and the residue then remaining was distilled under an oil pump vacuum. 17 g of product (=63% of theory) with a boiling point of 73° to 79° C. at 0.05 mbar were obtained.

The $^1$H-NMR spectrum showed characteristic bands at δ=2.39 to 2.81 ppm (m, 6H, CH$_2$); 3.38 ppm (d, 1H, CH) and 3.89 ppm (s, 3H, CH$_3$O) measured against tetramethylsilane as internal standard

Example 10

Preparation of
4-trifluoromethyl-4-nitrocyclohexan-1-one (formula
(II) in which m=3, B=oxygen,
$R^1=R^2=R^{1'}=R^{2'}$=hydrogen and A=vii) in which
$R^3=R^{3'}$=hydrogen)

27 g (0.1 mol) of the product prepared in accordance with Example 9 was boiled for 3 hours under reflux in 100 ml of 20% by weight hydrochloric acid. After cooling, the mixture was extracted with ether and the ether extract was washed with water and dried over sodium sulphate. After stripping off the ether, the residue was distilled. 14.8 g (=70% of theory) of the product quoted in the title, with a boiling point of 50° to 53° C. at 0.05 mbar, were obtained.

The $^1$H-NMR spectrum showed characteristic bands at $\delta=2.27$ to 2.75 ppm (m, 8H, CH$_2$) measured against tetramethylsilane as internal standard.

Example 11

Preparation of 1-trifluoromethyl-1-aminocyclohexane
(formula (II) in which m=3, B=hydrogen,
$R^1=R^2=R^{1'}=R^{2'}$=hydrogen and A=ix) in which
$R^3=R^{3'}$=hydrogen)

21.1 g (0.01 mol) of the product prepared in accordance with Example 10 were boiled for 2 hours under reflux with 0.3 mol of 85% by weight hydrazine solution and 22 g of finely powdered potassium hydroxide in 100 ml of triethylene glycol. The excess hydrazine hydrate was distilled off at a maximum temperature of 190° C. After 2 hours the evolution of nitrogen had ceased 500 ml of water were added to the reaction mixture, the resulting mixture was extracted several times with ether and the combined ether phases were dried over sodium sulphate. After stripping off the ether, 8.8 g (=53% of theory) of the product quoted in the title, with a boiling point of 112° to 114° C. at 20 mbar, were obtained.

The $^1$H-NMR spectrum showed characteristic bands at $\delta=1.3$ ppm (wide s, NH$_2$) and 2.16 to 2.65 ppm (m, 10H, CH$_2$) measured against tetramethylsilane as internal standard.

The $^{19}$F-NMR spectrum showed a characteristic band at $\delta-5.8$ ppm (s, CF$_3$) measured against CF$_3$COOH as external standard.

Example 12

Venturia test (apple), protective

A preparation of active compound was prepared by mixing 1 part by weight of the product prepared in accordance with Example 6 with 4.7 parts by weight of acetone and 0.3 parts by weight of alkylarylpolyglycol ether and diluting this concentrate with water to a concentration of 10 ppm. To test for protective activity, young plants were sprayed with the preparation of active compound until dripping wet. After the spray coating had dried on, the plants were inoculated with an aqueous conidia suspension of the apple scab causative organism (*Ventura inaequalis*) and then left to stand in an incubation cabin at 20° C. and 100% relative atmospheric humidity for 1 day.

The plants were then placed in a greenhouse at 20° C. and a relative atmospheric humidity of 70%.

Evaluation was carried out 12 days after the inoculation.

A degree of effectiveness of 62% compared with the untreated control resulted.

What is claimed is:

1. Fluorinated cyclohexane derivatives of the formula (I)

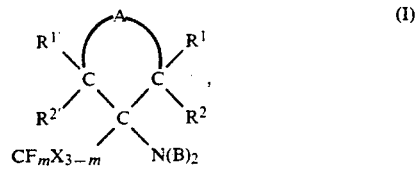

in which
A represents one of the following C$_3$-alkylene radicals

  i)

  ii)

  iii)

  iv)

  v)

  vi)

  vii)

  viii)

  ix)

X represents hydrogen, chlorine, bromine or methyl,
m represents 1, 2 or 3,
$R^1$, $R^2$, $R^3$, $R^{1'}$, $R^{2'}$ and $R^{3'}$ independently of one another in each case represent hydrogen, halogen, cyano or C$_1$- to C$_6$-alkyl
$R^4$ represents hydrogen or C$_1$- C$_6$-alkyl and Y represents COR$^{4'}$, cyano or nitro, wherein R$^{4'}$ is hydrogen or C$_1$- to C$_6$-alkyl.

2. Fluorinated cyclohexane derivatives of claim 1, in which in formula (I),

A represents i), ii), iv), vii) or viii),
X represents hydrogen or chlorine,
m represents 2 or 3,
R$^1$, R$^2$, R$^3$, R$^{1'}$, R$^{2'}$ and R$^{3'}$ independently of one another in each case represent hydrogen, halogen, or C$_1$- to C$_6$-alkyl,
Y represents a COR$^{4'}$ group in which R$^{4'}$=hydrogen, C$_1$- to C$_6$-alkyl, or a cyano group.

3. A fungicidal agent, which contains a compound of the formula (I) according to claim 1 as active compound and an inert carrier.

* * * * *

UNITED STATES PATENT AND TRADEMARK OFFICE
CERTIFICATE OF CORRECTION

PATENT NO. : 5,109,020

DATED : April 28, 1992

INVENTOR(S) : Negele, et al.

It is certified that error appears in the above-identified patent and that said Letters Patent is hereby corrected as shown below:

Col. 14, line 13   Delete " 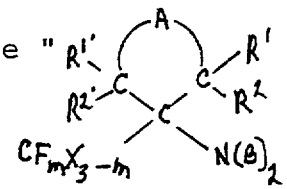 " and substitute

-- 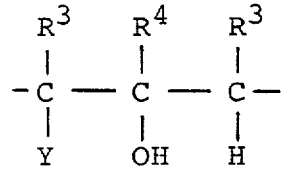 --

Col. 14, line 20   Delete "

$$-\underset{Y}{\overset{R^3}{\underset{|}{C}}} - \underset{OH}{\overset{R^4}{\underset{|}{C}}} - \underset{H}{\overset{R^3}{\underset{|}{C}}}-$$

" and substitute

UNITED STATES PATENT AND TRADEMARK OFFICE
CERTIFICATE OF CORRECTION

PATENT NO. : 5,109,020

DATED : April 28, 1992

INVENTOR(S) : Negele, et al.

It is certified that error appears in the above-identified patent and that said Letters Patent is hereby corrected as shown below:

Col. 14, line 20 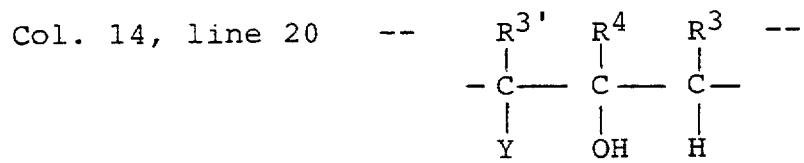

Signed and Sealed this

Sixteenth Day of August, 1994

Attest:

Attesting Officer

BRUCE LEHMAN

Commissioner of Patents and Trademarks